United States Patent [19]

Fucci

[11] Patent Number: 5,607,432
[45] Date of Patent: Mar. 4, 1997

[54] THREADED SUTURE ANCHOR RETRIEVER

[75] Inventor: Joseph Fucci, Palm Harbor, Fla.

[73] Assignee: Linvatec Corporation, Largo, Fla.

[21] Appl. No.: 343,749

[22] Filed: Jan. 23, 1995

[51] Int. Cl.$^6$ .................................................. A61B 17/00
[52] U.S. Cl. .......................... 606/104; 606/75; 606/232
[58] Field of Search ............................ 604/104, 232, 604/72–75, 86, 99, 187

[56] References Cited

U.S. PATENT DOCUMENTS

| | | | |
|---|---|---|---|
| 2,329,398 | 9/1943 | Duffy | 606/104 |
| 2,472,103 | 6/1949 | Giesen | 606/104 |
| 2,562,419 | 7/1951 | Ferris . | |
| 3,842,825 | 10/1974 | Wagner | 606/104 |
| 4,632,100 | 12/1986 | Somers et al. . | |
| 4,963,144 | 10/1990 | Huene | 606/104 |
| 5,100,471 | 3/1992 | Cerier et al. . | |
| 5,102,421 | 4/1992 | Anspach, Jr. . | |
| 5,141,520 | 8/1992 | Goble et al. . | |
| 5,156,616 | 10/1992 | Meadows et al. . | |
| 5,176,682 | 1/1993 | Chow . | |
| 5,207,679 | 5/1993 | Li . | |
| 5,224,946 | 7/1993 | Hayhurst et al. . | |
| 5,258,016 | 11/1993 | Di Poto et al. . | |
| 5,261,914 | 11/1993 | Warren . | |
| 5,268,001 | 12/1993 | Nicholson et al. . | |
| 5,312,438 | 5/1994 | Johnson . | |
| 5,370,662 | 12/1994 | Stone et al. | 606/75 |
| 5,375,956 | 12/1994 | Pennig | 606/73 |
| 5,441,502 | 8/1995 | Bartlett | 606/75 |

FOREIGN PATENT DOCUMENTS

| | | | |
|---|---|---|---|
| 827050 | 5/1981 | U.S.S.R. | 606/73 |
| 1053820 | 11/1983 | U.S.S.R. | 606/104 |
| 238724 | 9/1986 | U.S.S.R. | 606/104 |

OTHER PUBLICATIONS

Advertisement page from Arthroscopy, the Journal of Arthroscopic & Related Surgery, vol. 10, No. 4, 1994, showing PerFixation Screws from Instrument Makar, Inc.

Primary Examiner—Jeffrey A. Schmidt
Attorney, Agent, or Firm—Gene Warzecha

[57] ABSTRACT

A threaded bone anchor retriever and method for retrieving threaded bone anchors and the like from an implantation site. The anchor retriever is particularly suitable for retrieving threaded suture anchors during endoscopic surgical procedures. The retriever comprises an elongated shaft having an anchor engaging means at its distal tip for engaging the drive portion of the threaded anchor and for turning it in a direction to remove it from the implantation site. A concentric anchor engaging sleeve is adapted to move longitudinally relative to the elongated shaft in order to engage the threaded body of the anchor as it is removed from the implantation site. The invention includes a method for using the anchor retriever, particularly during endoscopic procedures, to remove anchors which may or may not have tissue growth overlying the implantation site.

10 Claims, 7 Drawing Sheets

THREADED SUTURE ANCHOR RETRIEVER

BACKGROUND OF THE INVENTION

1. Field of the Invention

The invention relates to the retrieval of suture anchors from a site of implantation in bone. More particularly, the invention relates to devices and methods for retrieving threaded suture anchors during either open or closed (endoscopic) surgical procedures.

2. Description of the Prior Art

In the course of certain surgical procedures, soft tissue is secured to a selected bone surface either directly, via some type of implant, or indirectly via an implant (i.e. an anchor) to which suture is attached, the suture then being tied to the soft tissue to hold it in place. Anchors may be used to attach soft tissue such as ligaments, tendons, muscles, etc. to a surface from which the soft tissue has become detached and may also be used to secure soft tissue to supplementary attachment sites for reinforcement. For example, in urological applications anchors may be used in bladder neck suspensions to attach a portion of the bladder to an adjacent bone surface. Such soft tissue attachment may be done during either open or closed surgical procedures, the latter being generally referred to as arthroscopic or endoscopic surgery. The terms "arthroscopic" and "endoscopic" may be used interchangeably herein and are intended to encompass arthroscopic, endoscopic, laparoscopic, hysteroscopic or any other similar surgical procedures performed with elongated instruments inserted through small openings in the body.

In procedures requiring suturing of soft tissue to bone, the suture is first anchored by so-called suture anchors to the bone before suturing of the soft tissue. The prior art includes numerous types of suture anchors adapted to be secured in the bone, sometimes directly in one step and sometimes in pre-drilled holes or tunnels. The term "suture anchor" is used broadly and will be understood to refer to devices having a similar structure even if material other than suture is connected to the device. Some prior art suture anchors are elongated and have annular ribs or radially extending barbs and are required to be pushed or hammered directly into bone or into a pre-formed bone tunnel (exemplified by U.S. Pat. Nos. 5,102,421 (Anspach, Jr.); 5,141,520 (Goble et al.); 5,100,417 (Cerier et al.); 5,224,946 (Hayhurst et al.) and 5,261,914 (Warren)). Pushing an anchor into place has the disadvantage of potential trauma and damage to surrounding bone tissue, and has limited applicability where the location of the bone tunnel or pre-drilled hole is not axially aligned with an arthroscopic portal to permit transmission of the impacting force through an impactor to the anchor. An impacted suture anchor is not easily removable without damaging the bone into which it has been placed. Consequently, threaded suture anchors are often used as exemplified by U.S. Pat. Nos. 5,156,616 (Meadows et al.) and 4,632,100 (Somers et al.). Depending upon the type of threaded anchor, the insertion procedure may enable direct threading of the anchor into the bone or it may sometimes require that a pilot hole first be drilled into the bone, the hole then either enabling an anchor to be screwed in or enabling threads to be tapped to receive the anchor.

In many instances, the suture anchor needs to be removed. For example, a particular implantation site may turn out to be unsuitable, either because of location or configuration, and the surgeon must either remove the anchor and place it elsewhere, or otherwise vary the procedure. Sometimes the anchor removal must occur after several months of healing so the anchor is overgrown with soft tissue and/or bone. With non-threaded prior art anchors there is no possibility of easily removing the inserted anchor and a second anchor must be inserted either in the same hole or a new hole. Accordingly, two (or possibly more) anchors may be left at the surgical site, only one of which is functional.

While threaded anchors are preferable in this regard because of the relative ease with which they may be removed from an implantation site, there is no known anchor retrieval device which facilitates the retrieval of a threaded anchor from an implantation site, particularly after several months of healing and bony ingrowth. Currently known removal procedures involve merely unscrewing a threaded anchor with the same screwdriver instrument used to implant it. However, even in endoscopic applications where the anchor is immediately removed after implantation, this is not as desirable as it sounds because once the anchor is removed from the bone it is not attached to the driver and may fall into the body cavity. The situation is even worse if the procedure is further complicated by removal after several months after implantation. Known methods for decorticating bone covering an anchor are relatively invasive and involve bone punches, picks, burrs, trephines, etc.

Many threaded suture anchors have a cylindrical threaded body with a drive portion at one end, the drive portion often having approximately the same diameter as the body. There is no "head" as one may find on some bone screws and this further limits the ease with which the anchor may be removed.

It is accordingly an object of this invention to provide a suture anchor retriever for removing a threaded suture anchor during an endoscopic surgical procedure.

It is further an object of this invention to provide a suture anchor retriever capable of removing a threaded anchor and holding it securely to facilitate its removal from the body through an access portal or cannula.

It is also an object of this invention to produce a suture anchor retriever capable of removing a threaded suture anchor from a site of implantation even after the anchor access may be somewhat obscured by soft tissue and/or bone. It is also an object to remove such a threaded suture anchor while minimizing and facilitating the removal of the surrounding bone.

It is another object of this invention to produce a suture anchor retriever capable of removing a threaded suture anchor having a headless, threaded cylindrical body.

SUMMARY OF THE INVENTION

These and other objects of this invention are achieved by the preferred embodiment disclosed herein which is a threaded anchor retriever for retrieving a threaded anchor from a site of implantation into which the threaded anchor has been turned. The embodiment comprises an elongated shaft having an elongated sleeve, concentrically situated about the shaft, the elongated sleeve adapted to move longitudinally relative to the elongated shaft. A primary anchor engaging means is disposed at the distal end of the elongated shaft for turning the anchor in a direction to remove it from the site of implantation. A secondary anchor engaging means is situated at the distal end of the sleeve for engaging the anchor. The invention further comprises means for advancing the secondary anchor engaging means distally while the anchor is being removed from the site of implantation by the primary anchor engaging means in order to engage the secondary anchor engaging means with the anchor. A holding means is provided for holding the anchor after it has been removed from the site of implantation.

A further object of this invention is achieved by a method for retrieving a threaded anchor from a site of implantation. The method comprises the steps of providing a threaded anchor retriever having a distal end adapted to engage a predetermined drive portion of the anchor, engaging the anchor with the distal end of the retriever and rotating it in a direction to disengage the anchor from the site of implantation. The method further comprises the steps of distally moving an elongated sleeve, concentrically disposed about the retriever, until the distal end of the sleeve engages the anchor and holding the anchor by the retriever to remove the anchor from the body.

DESCRIPTION OF THE PREFERRED EMBODIMENT

Figure 1:
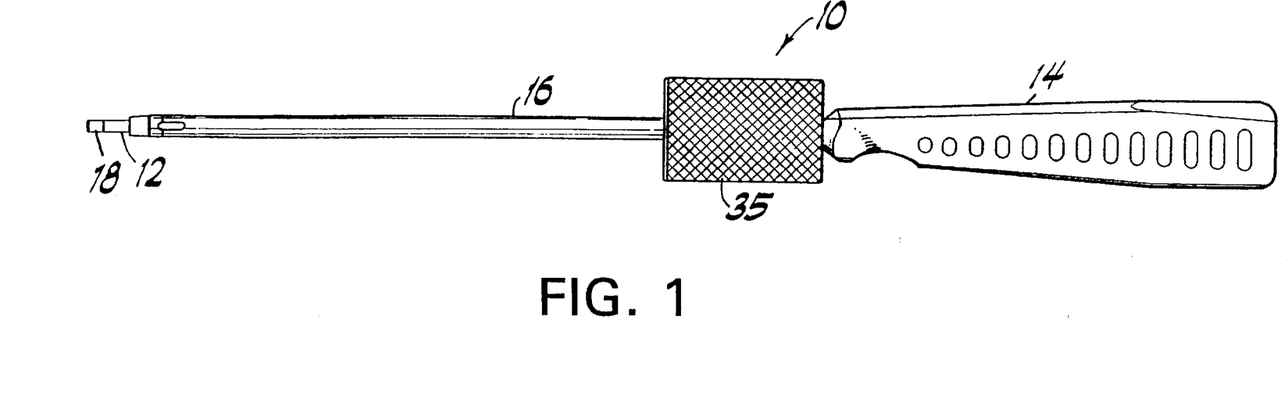
FIG. 1 is a side elevation view of an assembled suture anchor retriever constructed in accordance with the principles of this invention.
Figure 2:
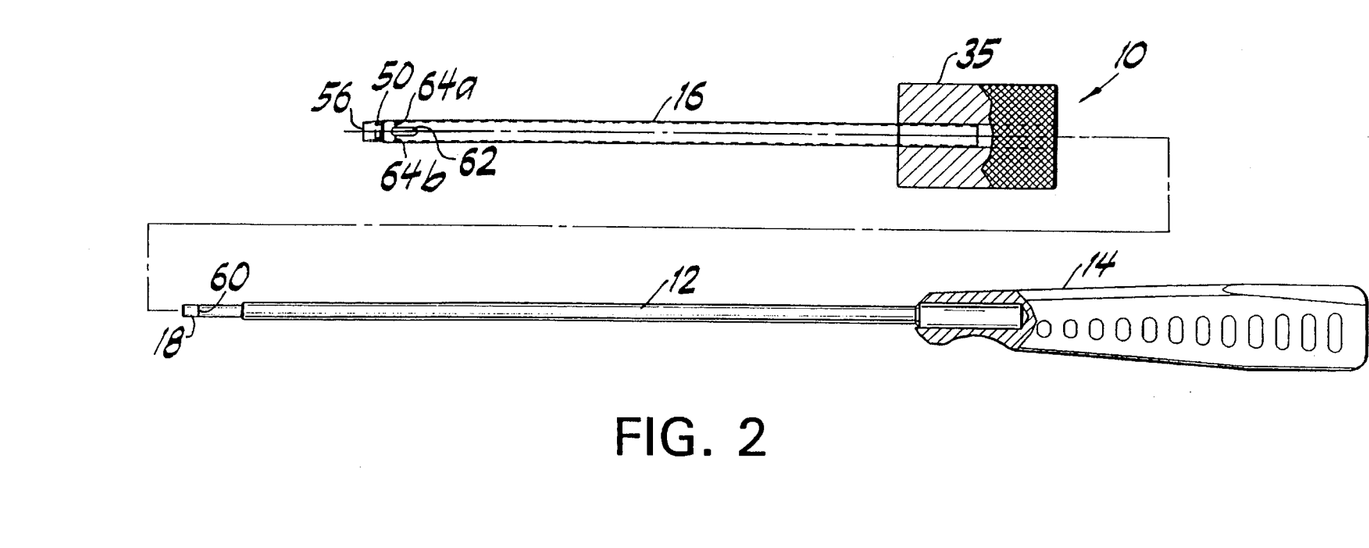
FIG. 2 is an exploded side elevation view of FIG. 1, partially in cross-section.

As shown in FIGS. 1 and 2, a suture anchor retriever 10 constructed in accordance with the principles of this invention comprises an elongated shaft 12 axially secured to the end of a handle 14. An elongated, cylindrical sleeve 16 is concentrically disposed about shaft 12 and, as will be understood below, is axially movable along shaft 12. The length and diameter of shaft 12 and sleeve 16 are sufficient to reach a selected surgical implantation site through either a portal or cannula. Retriever 10 has a primary anchor engaging means 18 at the distal tip of shaft 12 and is explained herein as being adapted for retrieval of a threaded suture anchor, an exemplary suture anchor 20 being best seen in FIG. 3.

Figure 3:
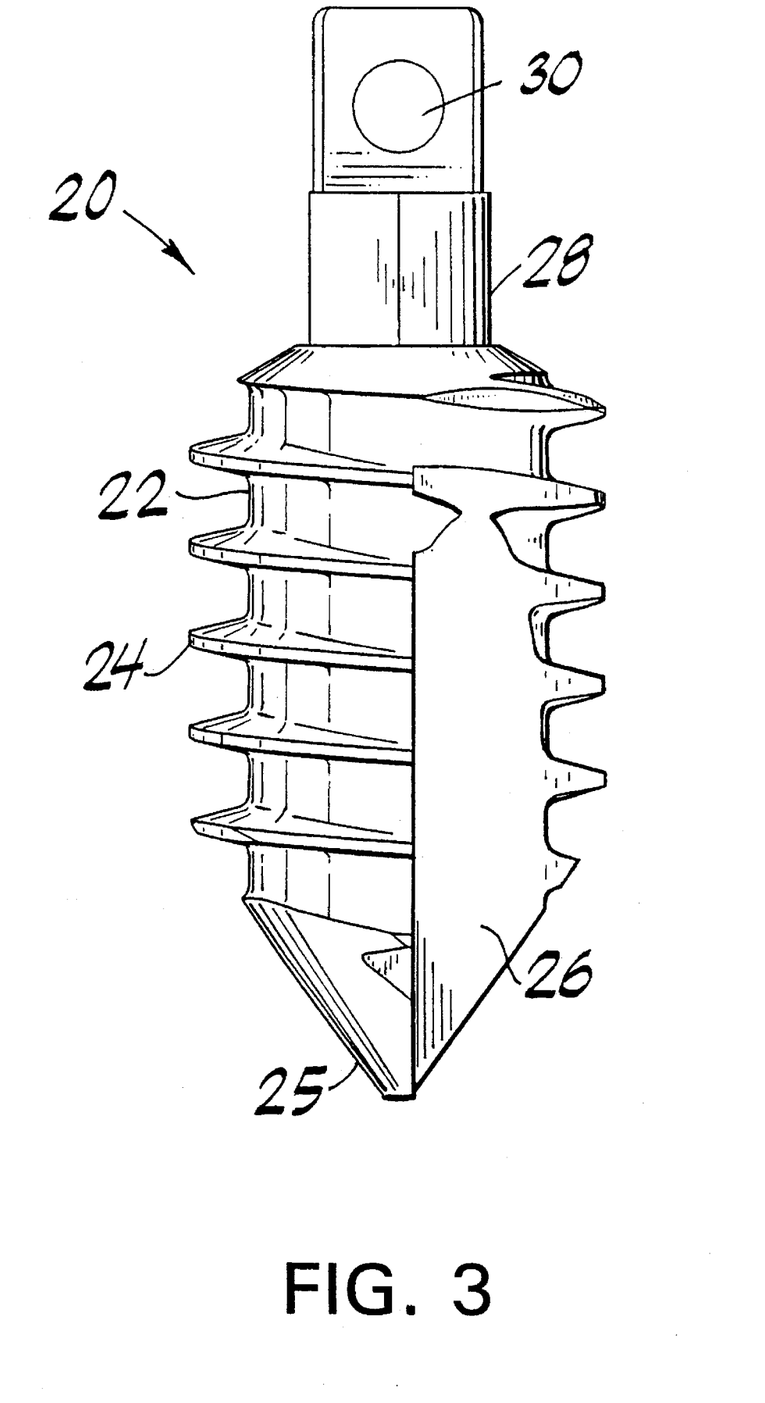
FIG. 3 is a side elevational view of a type of threaded suture anchor retrievable by the invention.

Exemplary threaded suture anchor 20 has a cylindrical body 22, a screw thread 24, a drill tip 25 having a flute 26 at the distal end of the body, an external drive portion 28 having a hexagonal cross-section and an eyelet 30 at the proximal end of the body for receiving suture (not shown). A similar self-drilling suture anchor is shown more particularly in U.S. Pat. No. 4,632,100 (Somers et al.) albeit without an eyelet. While the operation of the invention will be explained with reference to retrieving an anchor having a drive portion 28 with a plurality of externally facing surface having a hexagonal cross-section, it will be understood that an internally facing drive portion could easily be utilized by adapting engaging means 18 accordingly. Such an internally facing drive portion is shown in the aforementioned '100 patent and is essentially an axially aligned bore situated at the proximal end of the anchor.

Figure 4:
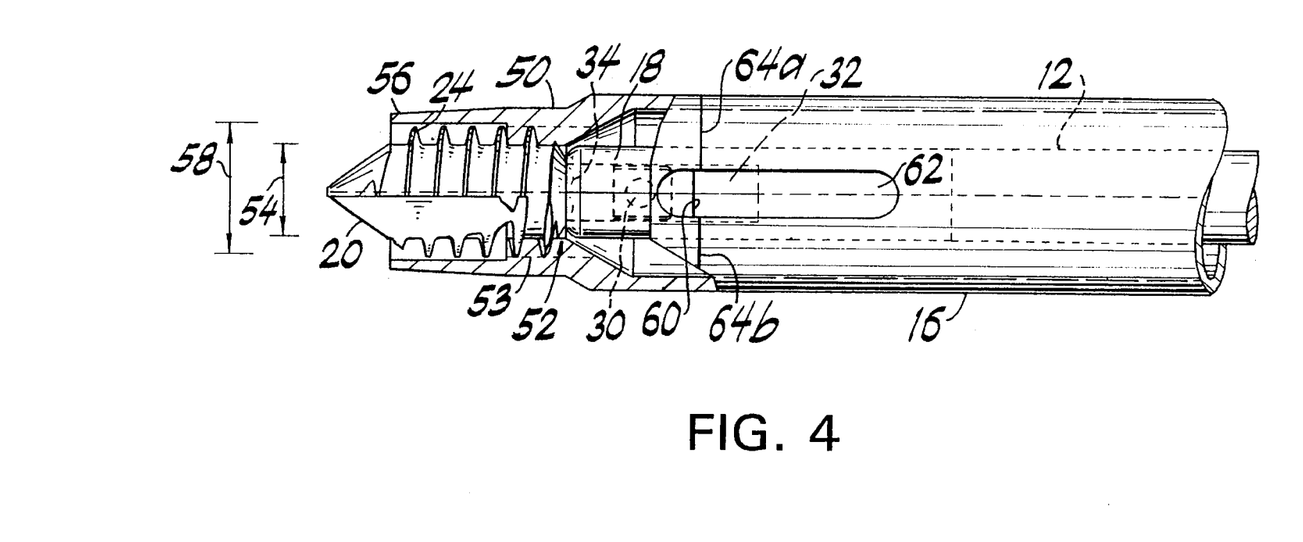
FIG. 4 is an exploded view showing an exemplary threaded suture anchor in engagement with the distal tip of the retriever of FIG. 1.

As best seen in FIGS. 2 and 4, primary anchor engaging means 18 at the distal end of shaft 12 has a profile or cross-section adapted to engage the drive portion of a corresponding threaded suture anchor. Engaging means 18 may be, for example, a longitudinal bore 32 of predetermined depth with a hexagonal cross-section sized to matingly receive corresponding hexagonal drive portion 28 of threaded suture anchor 20. The distal end of bore 32 is radiused at 34 to facilitate engagement of engaging means 18 with anchor 20.

Figure 5:
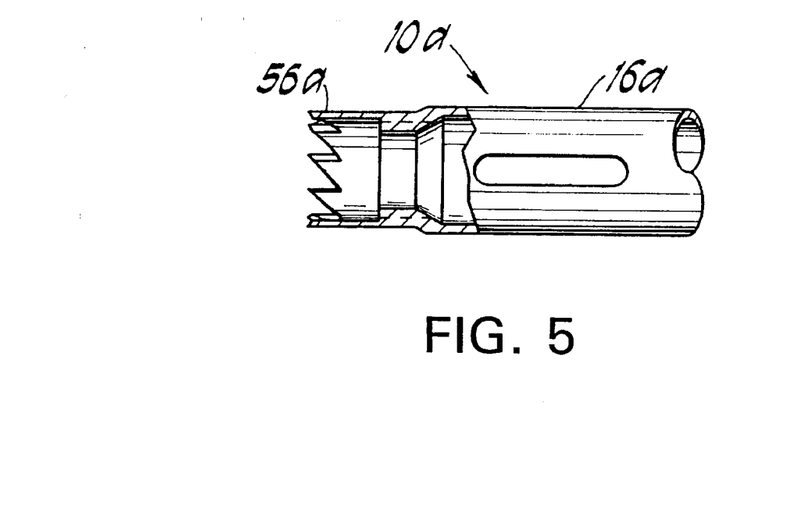
FIG. 5 shows an alternate embodiment of the distal tip of a suture anchor retriever, partially in cross-section.

Shaft 12 and sleeve 16 are longitudinally movable relative to each other in a controlled manner. In the preferred embodiment, shaft 12 has an outer diameter or cross-section adapted to slidably engage the internal diameter or cross-section of sleeve 16. In the preferred embodiment, both surfaces are cylindrical and the outer diameter of shaft 12 substantially equals the inner diameter of sleeve 16 in order to create a sliding fit. Other mechanisms may be utilized to enable relative longitudinal motion. (In some instances, depending upon the design of the anchor to be retrieved, relative rotation between shaft and sleeve may be desired and may be provided by cooperating longitudinally extending threads on the mating components.) The proximal end of elongated sleeve 16 is provided with a circular (or otherwise shaped) handle 35 to facilitate manipulation. The distal end 50 of elongated sleeve 16 (best seen in FIG. 4) is threaded on its internal surface with a secondary anchor engaging means 52 having a thread 53 of the same pitch as the thread 24 of anchor 20 in order to engage and hold the threaded anchor as it is being removed from an implantation site. While the preferred embodiment shows secondary anchor engaging means 52 as threaded, a non-threaded, soft material may be used in its place provided that it is soft enough or malleable enough to enable a rotating threaded anchor to become embedded in the material, and thereby frictionally captured. This type of capture may be achieved, for example, by providing sleeve 16 with a malleable polymeric insert or by making the entire sleeve from a suitable material. The internal diameter 54 of thread 53 is large enough to enable the body of shaft 12 to slidably pass therethrough to enable engaging means 18 to reach the anchor. End 50 also has circular, tapered, non-toothed coring tip 56 sized with an internal diameter 58 large enough to closely engage the anchor thread 24. The taper of end 50 facilitates placement of the tip in close proximity to the top of the hole in which the anchor is placed. As shown in FIG. 5, an alternate embodiment 10a of the invention may be made using sleeve 16a having a toothed coring tip 56a to facilitate tissue penetration and bone removal or decortication. The teeth may be oriented as shown to produce a cutting action upon rotation in one direction about the sleeve axis. Alternating teeth may also be used to produce cutting with an oscillating motion as will be understood below. The embodiment 10a of FIG. 5 is identical in all respects to retriever 10 of FIG. 1 except for the components having a suffix labelled "a", consequently, only the differentiated, toothed components are shown in FIG. 5. The components of the embodiment 10a will be referred to herein by the same numbers as those used to describe embodiment 10 of FIG. 1 except where the components have teeth.

Returning now to FIGS. 1 and 4, shaft 12 has an annular index line 60 near its distal tip and sleeve 16 has an elongated viewing window 62 near its distal end with a pair of adjacent, aligned indicia 64a and 64b. Window 62 enables a surgeon to view the position of either shaft 12 or of a threaded anchor being retrieved. The longitudinal position of shaft 12 when the index lines 60, 64a and 64b are aligned is such that the thread 24 of anchor 20 is engaged with thread 52 and the anchor is sufficiently disengaged from the implantation site to enable retriever 10 to be pulled out of the body.

Figure 6A:
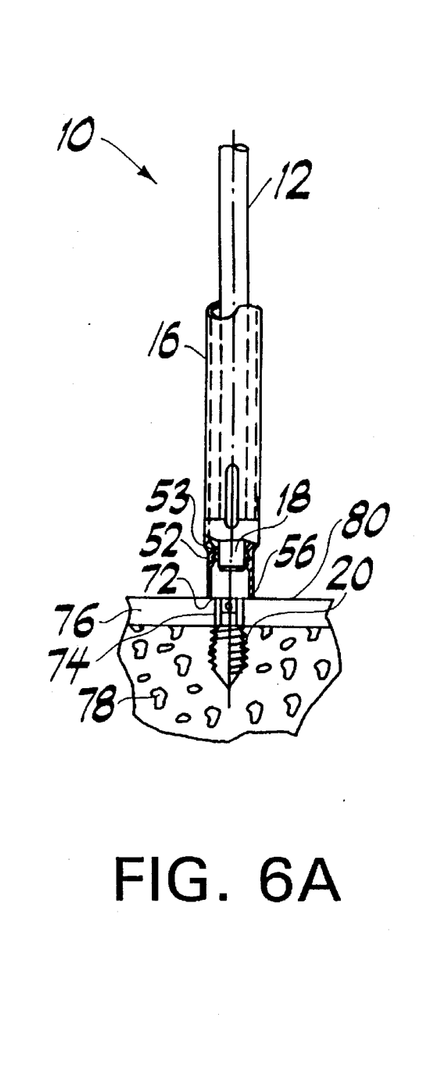
FIG. 6a–6d are sequential diagrammatic views showing the method of retrieving a threaded suture anchor using the retriever of FIG. 1.
Figure 6B:
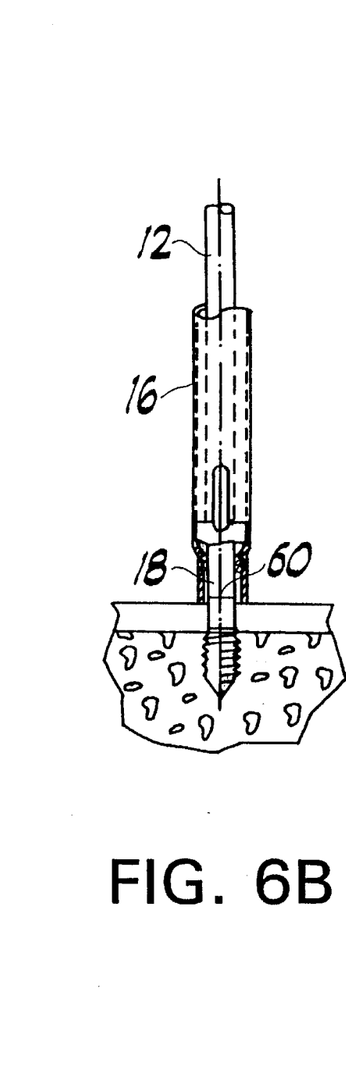
Figure 6C:
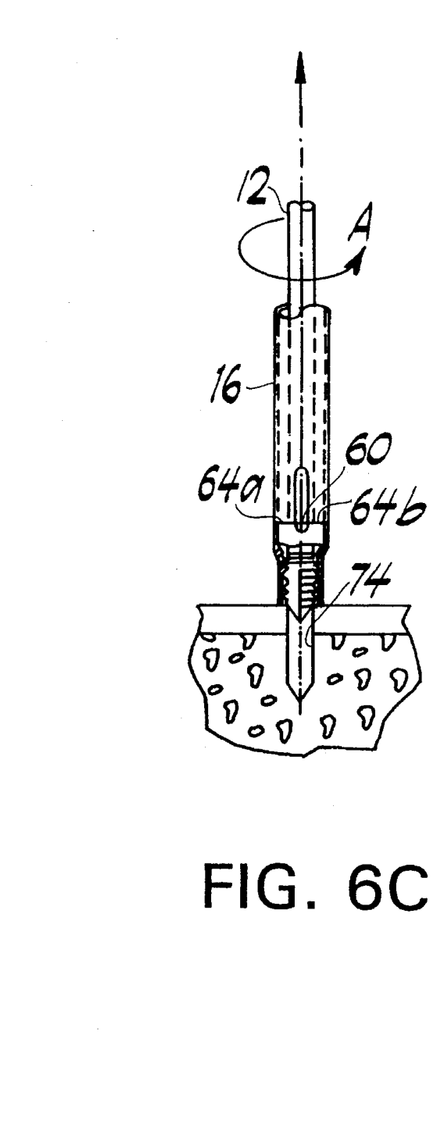
Figure 6D:
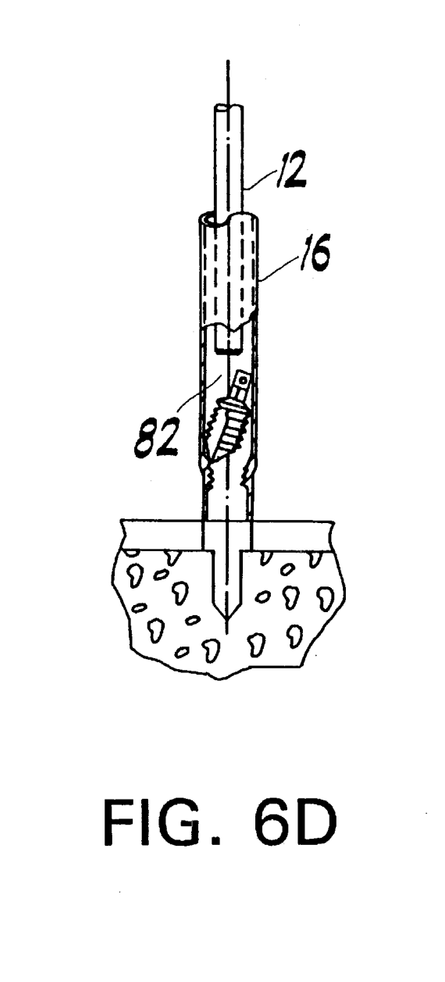

One method of using the invention is best seen in FIGS. 6a–6d which will be described with reference to the removal of exemplary threaded anchor 20 embedded at an implantation site 72. Implantation site 72 comprises a hole 74 (which may or may not be pre-drilled, depending upon the anchor being used) extending through cortical bone 76 into cancellous bone 78. The surface 80 of cortical bone 76 could in actuality have soft tissue (not shown) overlying it and suture would be tied through the eyelet of anchor 20 and the soft tissue to hold the soft tissue to the implantation site. In the drawings, the soft tissue and the suture have been omitted for clarity. FIGS. 6a–6d are descriptive of a method for retrieving anchor 20 shortly after its implantation at site 72. At this point in time, the cortical bone has not healed sufficiently to cover the hole 74 and envelop screw 20. Suture anchor retriever 10 may, therefore, be directly engaged with the anchor without the necessity of decorticating any bone or tissue overlying the anchor. As shown in FIG. 6a, under arthroscopic visualization (not shown) the distal end of coring tip 56 of sleeve 16 is placed and held adjacent site 72 above and in line with the axis of anchor 20. Any sutures extending from the anchor eyelet should not interfere with operation of the device, but may be removed if desired. Then, as shown in FIG. 6b, shaft 12 and, consequently, primary anchor engaging means 18 is pushed distally relative to sleeve 16 in order to engage it with drive portion 28 of anchor 20. As shown in FIG. 6c, sleeve 16 and, consequently, secondary anchor engaging means 52 is then held stationary while primary anchor engaging means 18 is turned in a direction A to move anchor 20 proximally and eventually into engagement with the thread 53 of secondary anchor engaging means 52 on the interior surface of sleeve 16. Relative rotation between the primary and secondary anchor engaging means causes the anchor to back out of hole 74 and seat more and more securely in thread 53, until, as shown in FIG. 6c by aligned indicia 60, 64a and 64b, the anchor is fully disengaged from bone. Further turning of shaft 12 will, as shown in FIG. 6d, move anchor 20 further into the interior 82 of sleeve 16 where it becomes fully entrapped in order to assure its safe removal from the body.

Figure 7A:
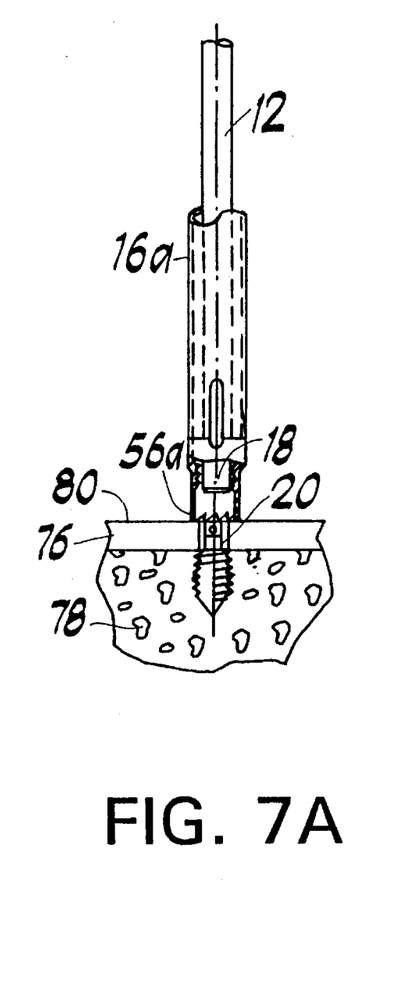
FIGS. 7a–7f are sequential diagrammatic views of an alternate method of retrieving a suture anchor with the retriever of FIG. 5 using a toothed outer sheath for decorticating the surrounding bone.
Figure 7B:
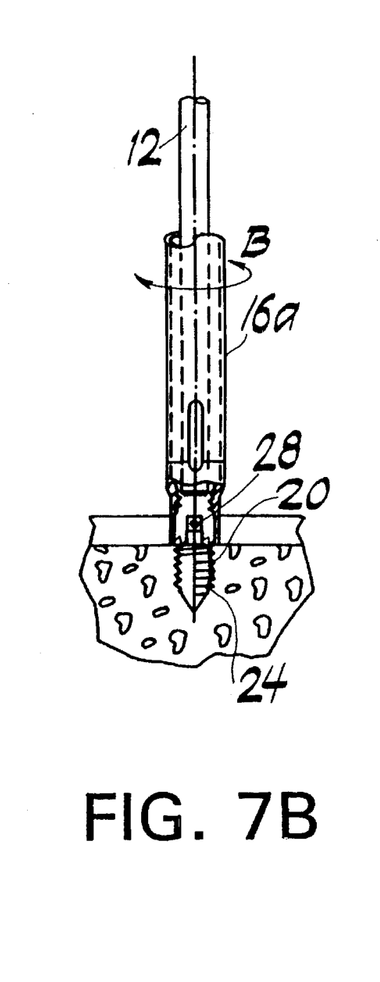
Figure 7C:
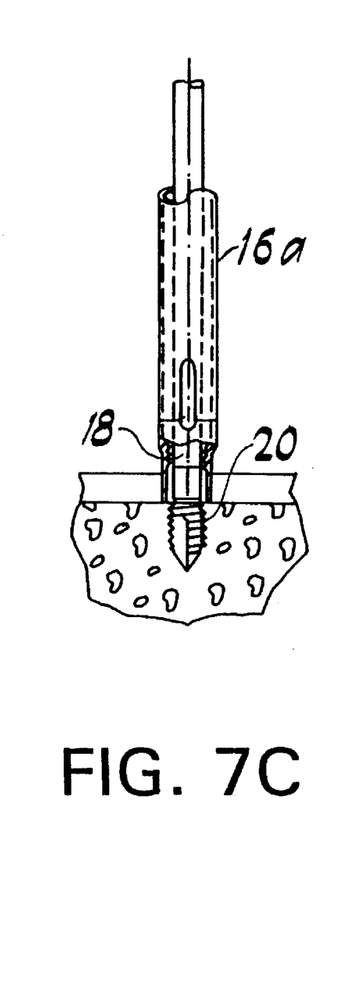
Figure 7D:
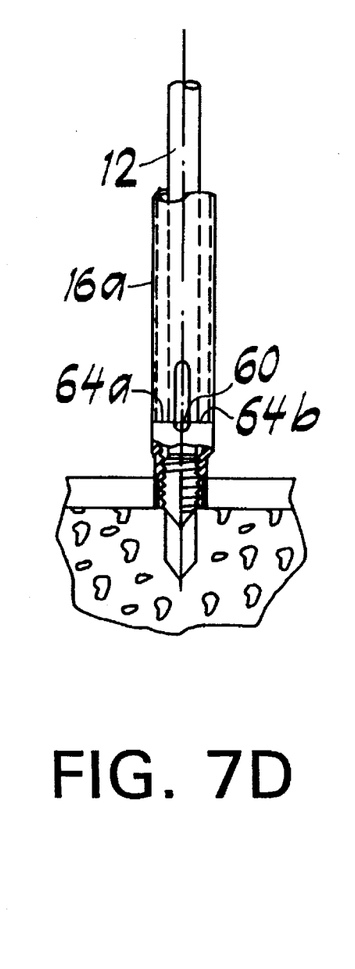
Figure 7E:
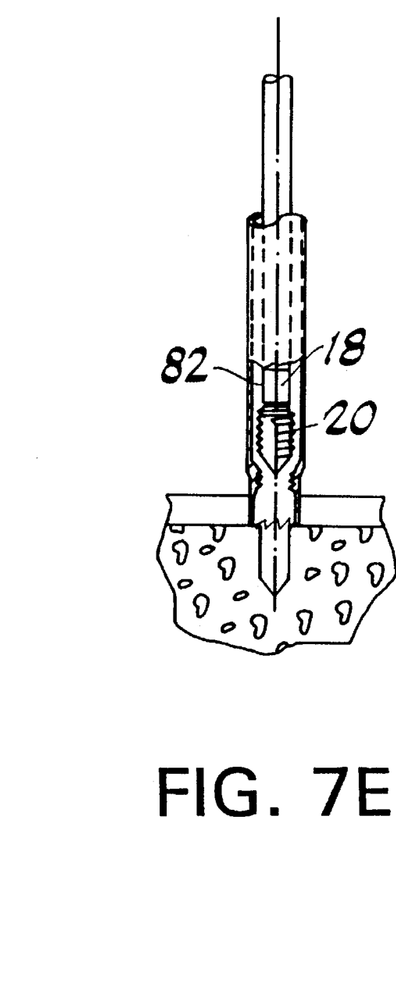
Figure 7F:
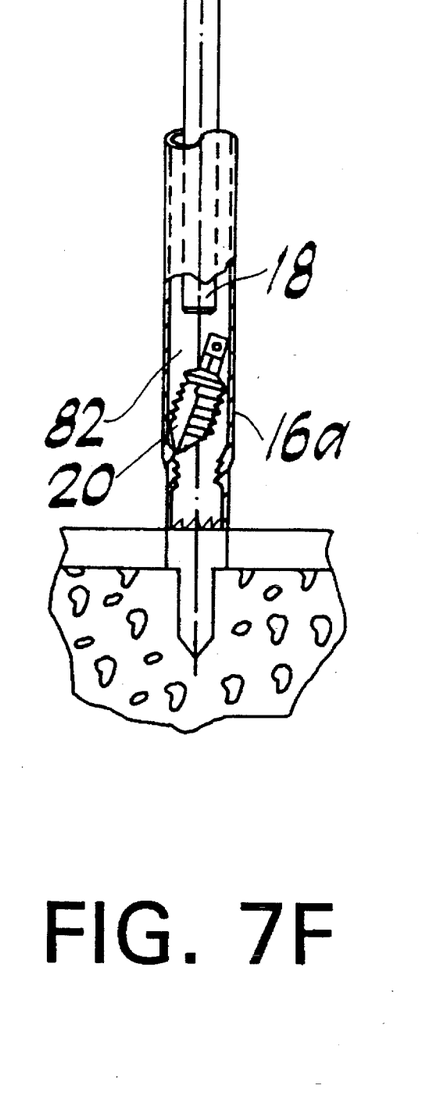

Referring now to FIGS. 7a–7f, an alternate method of retrieving a threaded suture anchor is shown using the device shown in FIG. 5. While this method is similar to that described by reference to FIGS. 6a–6d, this alternate method is suitable in instances where the threaded anchor has been embedded for a time sufficient to have tissue growth overlying the anchor. As shown in FIG. 7a, the toothed coring tip 56a referred to in FIG. 5 is first placed above anchor 20 as with the previously described method. In order to provide access for primary anchor engaging means 18 to anchor 20, sleeve 16a must first be advanced, for example, by an oscillatory motion B through bone and/or soft tissue into a position over anchor 20 as shown in FIG. 7b. This may also be done by either turning sleeve 16a in one direction or pushing it into place or otherwise removing a core of bone or soft tissue above anchor 20. In certain instances, even though primary anchor engaging means 18 can be engaged with the drive portion of the anchor, coring tip 56a may need to be inserted deeper than through the soft tissue and/or cortical layer in order to relieve pressure on the sides of the anchor by coring out a portion of bone around anchor thread 24. The "cored-out" bone and/or tissue debris is not shown for clarity, but it will be understood that this debris is not an impediment to proper operation of the invention since it can be readily removed if necessary. Once the drive portion 28 of anchor 20 is accessible, primary engaging means 18 is pushed distally relative to sleeve 16a as shown in FIG. 7c until it becomes engaged with the drive portion of the anchor. Primary engagement means 18 may then be turned as shown in FIG. 7d in a direction to begin removing anchor 20. Alignment line 60 on shaft 12 lines up with indicia 64 and 64b on sleeve 16a when the anchor is fully disengaged. Sleeve 16a is held stationary while primary engagement means 18 is rotated to move anchor 20 proximally relative to sleeve 16a until it becomes fully enclosed within the interior 82 of sleeve 16a as shown in FIG. 7e. Anchor 20 may fall off primary engagement means 18 as shown in FIG. 7f, although it will still be retained within the interior and may be safely removed from the body.

While the preferred embodiment disclosed herein is intended to operate to retrieve a threaded anchor having a spiral thread extending longitudinally along the cylindrical exterior surface of a threaded anchor, the invention could also be made to operate with other "thread" configurations such as, for example, a plurality of spiral ribs none of which extends 360° completely around the cylindrical surface.

The preferred embodiment disclosed herein is in the form of a rigid, elongated retriever. The invention could equally be made flexible to enable the shaft and concentric, slidable sleeve to be bent along a non-linear path to facilitate removal of threaded suture anchors which cannot be easily engaged by a rigid device. Furthermore, while the preferred embodiment of the retriever is shown solid, it could also be made cannulated to assist in guiding the retriever to the desired implantation site.

It will be understood by those skilled in the art that numerous improvements and modifications may be made to the preferred embodiment of the invention disclosed herein without departing from the spirit and scope thereof.

What is claimed is:

1. A threaded anchor retriever for endoscopically retrieving a threaded anchor from a site of implantation into which the threaded anchor has been turned, the threaded anchor having a threaded body for being embedded at the site when turned in a first direction and a drive means for turning the threaded body, comprising:

an elongated shaft having a proximal end and a distal end;

a primary anchor engaging means disposed at said distal end of said elongated shaft for engaging said drive means to thereby turn said anchor in a direction opposite said first direction in a direction to remove it from said site of implantation;

a predetermined fixed diameter secondary anchor engaging means disposed adjacent said primary anchor engaging means for automatically engaging the threaded body of said anchor as said anchor is turned in said opposite direction and moves relative to said secondary anchor engaging means;

means for moving said primary and secondary anchor engaging means in opposite directions relative to each other in order to remove said anchor from said site of implantation by said primary anchor engaging means while urging said anchor into engagement with said secondary anchor engaging means.

2. A threaded anchor retriever according to claim 1 further comprising means, associated with said elongated shaft, for holding said anchor after it has been removed from the site of implantation.

3. An anchor retrieval system for retrieving a threaded anchor from a site of implantation into which the threaded anchor has been turned, comprising: a threaded anchor having a threaded body for being embedded at the site when turned in a first direction and a drive means for turning the threaded body into the site; a retriever comprising an elongated shaft having a proximal end and a distal end;

an elongated sleeve, having a proximal end and a distal end, concentrically situated about said shaft, said elongated sleeve adapted to move longitudinally relative to said elongated shaft;

a primary anchor engaging means disposed at said distal end of said elongated shaft for engaging said drive means to thereby turn said anchor in a direction opposite said first direction to remove it from the site of implantation;

a predetermined fixed diameter secondary anchor engaging means disposed at the distal end of said sleeve for automatically engaging the threaded body of said anchor as said anchor is turned in said opposite direction and moves relative to said secondary anchor engaging means;

means for moving said primary and secondary anchor engaging means in opposite directions relative to each other in order to remove said anchor from the site of implantation by said primary anchor engaging means while urging said anchor into engagement with said secondary anchor engaging means;

means at the distal end of said elongated sleeve for holding said anchor after it has been removed from the site of implantation.

4. A threaded anchor retriever according to claim 3 in combination with a threaded anchor having a drive means comprising an axially aligned elongated extension with a predetermined non-circular cross-section, said primary anchor engaging means having an axially aligned recess with a corresponding, mating predetermined non-circular cross-section.

5. A threaded anchor retriever according to claim 3 wherein said secondary anchor engaging means has the same thread pitch as the threaded body of said anchor.

6. A threaded anchor retriever according to claim 3 wherein said secondary anchor engaging means comprises a non-threaded material capable of frictionally engaging said anchor.

7. A method for retrieving a threaded anchor from a site of implantation comprising the steps of:

providing an elongated anchor retrieval shaft having a proximal end and a distal end, said distal end adapted to engage a predetermined drive portion of said anchor;

engaging said anchor with said distal end of said retrieval shaft;

rotating said retrieval shaft in a direction to move said anchor proximally to disengage said anchor from its site of implantation;

providing a sleeve, concentrically disposed about said retrieval shaft, said sleeve having a predetermined fixed diameter anchor engaging portion adjacent the distal end thereof;

producing relative longitudinal motion between said sleeve and said anchor until the anchor engaging portion of said sleeve engages said anchor;

holding said anchor;

removing said anchor from the body.

8. A method according to claim 7 further comprising the step of:

rotating said retrieval shaft to move said anchor proximally to disengage the anchor from its site of implantation while causing simultaneous relative motion of said elongated sleeve distally to engage it with said anchor.

9. A method according to claim 7 further comprising the step of providing an elongated extension on said sleeve to enable it to be manipulated from a point remote from the site of implantation.

10. A method according to claim 7 further comprising the step of:

holding said anchor in said distal end of said sleeve.

* * * * *